(12) United States Patent
Muyari

(10) Patent No.: US 8,740,899 B2
(45) Date of Patent: Jun. 3, 2014

(54) OPERATION SECTION STRUCTURE OF TREATMENT INSTRUMENT FOR ENDOSCOPIC USE

(75) Inventor: Yuta Muyari, Tokyo (JP)

(73) Assignee: Olympus Medical Systems Corp. (JP)

( * ) Notice: Subject to any disclaimer, the term of this patent is extended or adjusted under 35 U.S.C. 154(b) by 1082 days.

(21) Appl. No.: 12/184,530

(22) Filed: Aug. 1, 2008

(65) Prior Publication Data

US 2009/0036737 A1 Feb. 5, 2009

(30) Foreign Application Priority Data

Aug. 2, 2007 (JP) ............... P2007-202103

(51) Int. Cl.
*A61B 18/14* (2006.01)
*A61B 17/00* (2006.01)

(52) U.S. Cl.
CPC ..... *A61B 18/1492* (2013.01); *A61B 2018/1475* (2013.01); *A61B 2017/00415* (2013.01)
USPC .............................. 606/46; 606/51

(58) Field of Classification Search
CPC ........... A61B 18/1445; A61B 18/1492; A61B 2018/00077; A61B 2018/1407; A61B 2018/144; A61B 2018/1475; A61B 18/14; A61B 2018/00601; A61B 2018/00595; A61B 2017/00389; A61B 2017/00415; A61B 2017/00424; A61B 2017/00438
USPC ............... 606/113, 47, 46; 600/106, 121, 127
See application file for complete search history.

(56) References Cited

U.S. PATENT DOCUMENTS

| | | | |
|---|---|---|---|
| 5,066,295 A | 11/1991 | Kozak et al. | |
| 6,352,539 B1 * | 3/2002 | Avellanet | 606/113 |
| 7,008,420 B2 * | 3/2006 | Okada | 606/47 |
| 7,052,495 B2 * | 5/2006 | Smith | 606/47 |
| 2004/0172018 A1 * | 9/2004 | Okada | 606/46 |
| 2005/0215996 A1 | 9/2005 | Ouchi | 606/46 |

FOREIGN PATENT DOCUMENTS

| | | |
|---|---|---|
| EP | 1 862 121 A1 | 12/2007 |
| EP | 1 864 621 A1 | 12/2007 |
| JP | 57-145654 | 9/1982 |
| JP | 10-223344 | 8/1998 |
| JP | 2002-253563 | 9/2002 |
| JP | 2004-121485 | 4/2004 |

OTHER PUBLICATIONS

European Search Report dated Oct. 31, 2008.

(Continued)

*Primary Examiner* — Michael Peffley
*Assistant Examiner* — Thomas Giuliani
(74) *Attorney, Agent, or Firm* — Ostrolenk Faber LLP

(57) ABSTRACT

An operation section structure of a treatment instrument for endoscopic use has: a hook knife inserted into a body cavity; a wire having a distal end connected to the hook knife; a tubular flexible sheath provided to an outer periphery of the wire; a current-carrying plug having a main unit having a distal end connected to the sheath; a sliding member made of a conductive material and having a proximal end of the wire fixed thereto, the sliding member being capable of sliding on the main unit in longitudinal direction; a operation member capable of freely rotating in circumferential direction of the operation member; and attached to the sliding member; and a conductive section provided to the operation member, the conductive section being made of a conductive material providing conductivity by making contact with the sliding member. This configuration can rotate the distal end structure easily.

9 Claims, 8 Drawing Sheets

(56) References Cited

OTHER PUBLICATIONS

Office Action issued by the Japanese Patent Office on Mar. 27, 2012 in connection with corresponding Japanese Patent Application No. 2007-202103.

Translation of Office Action issued by the Japanese Patent Office on Mar. 27, 2012 in connection with corresponding Japanese Patent Application No. 2007-202103.

* cited by examiner

US 8,740,899 B2

OPERATION SECTION STRUCTURE OF TREATMENT INSTRUMENT FOR ENDOSCOPIC USE

BACKGROUND OF THE INVENTION

1. Field of the Invention

The present invention relates to an operation section structure of a treatment instrument for endoscopic use inserted into an operation channel of an endoscope apparatus.

2. Background Art

Treatment instruments for endoscopic use inserted into an operation channel provided along a scope of an endoscope apparatus are commonly known (see Japanese Unexamined Patent Application, First Publication No. S57-145654) for conducting various treatments. The distal end mechanism of these procedure instruments differs in accordance with the purpose of the treatment, e.g., sampling, or tissue cautery. Sometimes, procedure instruments, in an attempt to obtain more desirable correlation between a target site tissue and the distal end mechanism, require rotatable distal end mechanisms in many cases.

A conventional treatment instrument for endoscopic use in this case requires the rotation of a slider having a wire fixed to the distal end mechanism and to the wire, and a main unit having a tubular sheath surrounding the outer periphery of the wire and fixed to the main unit.

However, the aforementioned operation has an annoying drawback because the operator must release their hand from the main unit and re-grasp the endoscope apparatus to provide rotation.

Another treatment instrument for endoscopic use has a high-frequency power supply for supplying high-frequency electric current to a distal end structure thereof, and in many cases, a cable connects the high-frequency power supply with a current-carrying plug provided to the slider. The aforementioned operation will meet a difficult problem because the use of such a procedure instrument that rotates the main unit causes the cable to become entangled around the main unit.

SUMMARY OF THE INVENTION

The present invention was conceived in consideration of the aforementioned circumstances, and an object thereof is to provide a operation section structure of a treatment instrument for endoscopic use that can rotate a distal end structure easily.

The present invention is an operation section structure of a treatment instrument for endoscopic use which includes: a distal end mechanism inserted into a body cavity for conducting various intervention; a wire having a distal end connected to the distal end mechanism; a tubular flexible sheath provided to an outer periphery of the wire; a main unit having a distal end connected to the sheath; a sliding member made of a conductive material, a proximal end of the wire being connected to the sliding member, the sliding member being capable of sliding on the main unit in the longitudinal direction; an operating member attached to the sliding member, the operating member being capable of rotating relative to the sliding member in the circumferential direction; and a current-carrying section provided to the operating member and having a conductive section formed by a conductive material providing conductivity by making contact with the sliding member.

According to the operation section structure of the treatment instrument for endoscopic use of the present invention, operating and rotating the main unit causes the sliding member, the wire, and the distal end mechanism to rotate without rotating the operating member.

A handle capable of freely rotating around the main unit as a rotational axis may be provided to a proximal end of the main unit.

The conductive section may be formed by bending a conductive plate material having bending lines extending in a sliding direction of the sliding member. In addition, the conductive section may be formed to include a spring made of a conductive material.

The treatment instrument for endoscopic use may be disposed inward relative to the sheath and outward relative to the wire. A distal end may be fixed to the distal end mechanism. A proximal end may have a coil sheath fixed to the main unit and be incapable of rotating. The sliding member may be configured so that a first member and a second member dispose the main unit to be fixed therebetween.

According to the operation section structure of the treatment instrument for endoscopic use of the present invention, rotating the main unit while holding the operation section allows the distal end mechanism to be rotated easily without rotating the operating member.

PREFERRED EMBODIMENTS

An treatment instrument for endoscopic use provided with an operation section structure according to a first embodiment of the present invention will be explained with reference to FIGS. 1 to 5.

Figure 1:
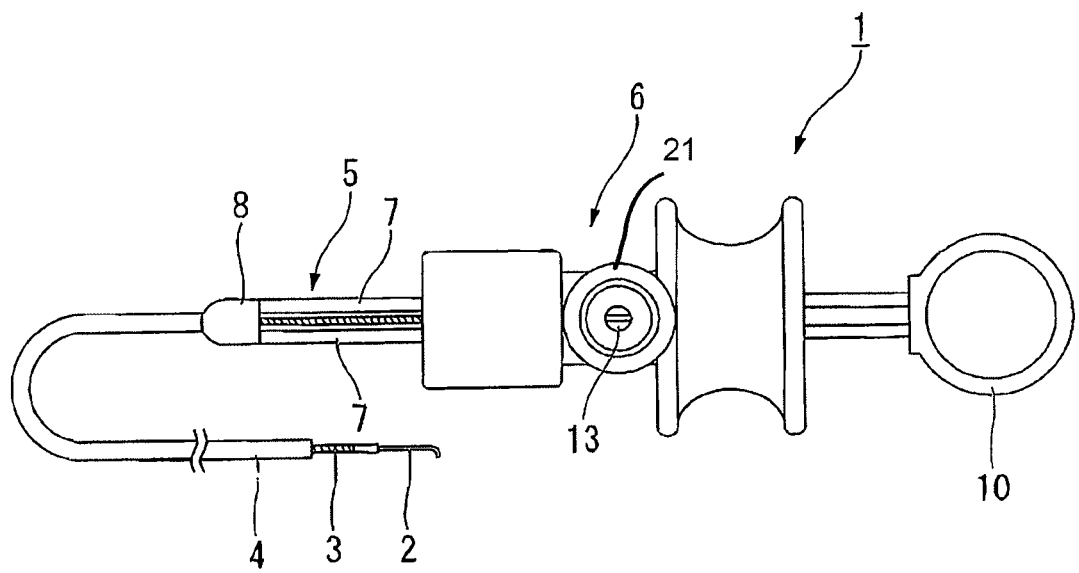
FIG. 1 is a plan view of a treatment instrument for endoscopic use provided with an operation section structure according to a first embodiment of the present invention.

FIG. 1 is a plan view of a endoscopic-use instrument 1 provided with the operation section structure of the present embodiment. The endoscopic-use instrument 1 is provided with: a wire 3 having a hook knife 2 (distal end mechanism) attached to the distal end of the wire 3; a sheath 4 surrounding the outer periphery of the wire 3; a main unit 5 having the proximal end of the sheath 4 fixed thereto; and an operation section 6 having the proximal end of the wire 3 fixed thereto.

The hook knife 2 is formed by bending a head of a bar metal member by a length of 1.5 mm in right angle. The proximal end of the hook knife 2 is fixed to the wire 3. The wire 3 made of metal, e.g., stainless steel is inserted through an elastic tubular sheath 4 made from resin, etc.

Figure 2:
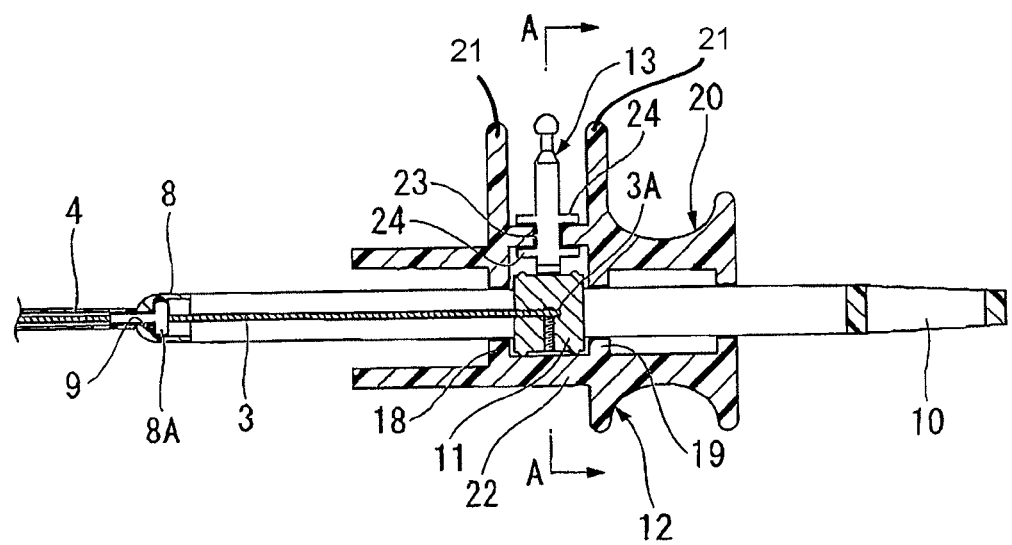
FIG. 2 is a cross sectional view showing the treatment instrument for endoscopic use.

The main unit 5 made of resin, etc. includes a pair of paralelly-disposed two-bar lateral wall sections 7. A sheath fixture section 8 is fixed to the tip of the lateral wall section 7 by an engagement mechanism, e.g., a groove, not shown in the drawing. As shown in FIG. 2, the proximal end of the sheath 4 is connected to the sheath fixture section 8 rotatably via a connecting member 8A disposed in the sheath fixture section 8.

A through-hole 9 is provided to the distal end of the sheath fixture section 8. The wire 3 passing through the sheath 4, the connecting member 8A, and the through-hole 9 is introduced between the lateral wall sections 7. A finger during operation is placed in a finger hook ring handle 10 provided to the proximal end of the main body 7.

The operation section 6 is provided with a freely slidable sliding member 11 attached to the main unit 5; a freely rotatable operation member 12 attached to the outer periphery of the sliding member 11; and a current-carrying plug (current-carrying section) 13 attached to the operation member 12 in configuration.

Figure 3:
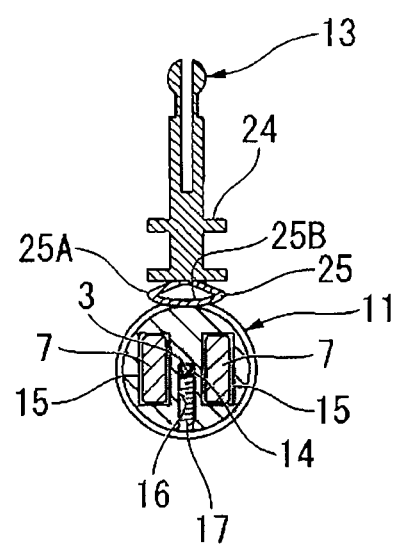
FIG. 3 is a cross-sectional view of a current-carrying plug and a sliding member along the line A-A in FIG. 2.

The substantially cylindrical sliding member 11 is made of a conductive material, e.g., metal, etc. As shown in FIG. 3, the wire 3 is fixed in a fixture hole 14 provided in the center of a plane section of the sliding member 11. A pair of sliding holes 15 provided laterally relative to the fixture hole 14 allows the lateral wall sections 7 of the main unit to pass therethrough.

The lateral wall sections 7 of the main unit 5 are passed through the sliding holes 15 of the sliding member 11. A proximal end 3A of the wire 3 passing through the through-hole 9 of the sheath fixture section 8 is inserted into the fixture hole 14. The proximal end 3A is fixed to the sliding member 11 by a screw 17 screwed into a screw hole 16 reaching from the outer periphery of the sliding member 11 to the fixture hole 14. That is, the sliding member 11 fixed to the wire 3 unitarily and fixed to the main unit 5 is capable of sliding at the lateral wall sections 7.

The operation member 12, made of resin, etc., has a front wall section 18 provided distally relative to the sliding direction of the sliding member 11 and a rear wall section 19 provided proximally relative to the sliding direction of the sliding member 11; a finger hook section 20 provided in the vicinity of the handle 10 relative to the rear wall section 19; and a plug mount section 21 provided between the front wall section 18 and the rear wall section 19 in configuration.

The front wall section 18 and the rear wall section 19 are disks each formed to have a hole having substantially the same diameter as that of the main unit 5. The distally located front wall section 18 and the proximally located rear wall section 19 fix the sliding member 11 therebetween in the sliding direction of the sliding member 11. A cylindrical section 22 connecting the front wall section 18 to the rear wall section 19 unitarily surrounds the outer periphery of the sliding member 11 between these components.

The cylindrical finger hook section 20, made of resin, etc. and having a hole having substantially the same diameter as that of the main unit 5, is provided together with the rear wall section 19 unitarily in the vicinity of the handle 10 relative to the rear wall section 19.

The cylindrically-formed plug mount section 21 extends outward from the outer periphery of the cylindrical section 22 in the radial direction. A mount hole 23 allowing a current-carrying plug 13 to be mounted thereinto is provided on the outer periphery of the cylindrical section 22 surrounded by the plug mount section 21.

The distal end of the bar-shaped current-carrying plug 13 made of conductive material is connected to a power supply which is not shown in the drawing. The current-carrying plug 13 inserted and mounted in the mount hole 23 of the cylindrical section 22 is fixed in the cylindrical section 22 by a flange fixture section 24. A conductive tongue piece (conductive section) 25 provided to the end section in the vicinity of the sliding member 11 of the current-carrying plug 13 obtains conductivity between the current-carrying plug 13 and the sliding member 11.

Two ends of the conductive tongue piece 25 made of a conductive plate material are fixed to the current-carrying plug 13 in a substantial ring shape. The conductive tongue piece 25 is bent along bending lines 25A extending in the axial line direction of the cylindrical section 22 in configuration. Bending work provided to the portion between the bending lines 25A forms a curved surface 25B projecting toward the sliding member 11. Resilience attempting to restore the bending line 25A into the initial shape urges the curved surface 25B to make contact with the sliding member 11.

The operation member 12 and the current-carrying plug 13 as a whole fixed to the sliding member 11 are capable of freely rotating around the axial line direction of the main unit 5 relative to the main unit 5 and the sliding member 11.

Movement of the endoscopic-use instrument 1 having the aforementioned configuration in use will be explained as follows.

In the beginning, the insertion section of an endoscope is inserted into the body cavity of a patient, etc., and the distal end of the insertion section is moved to the vicinity of an object tissue for intervention.

Figure 4:
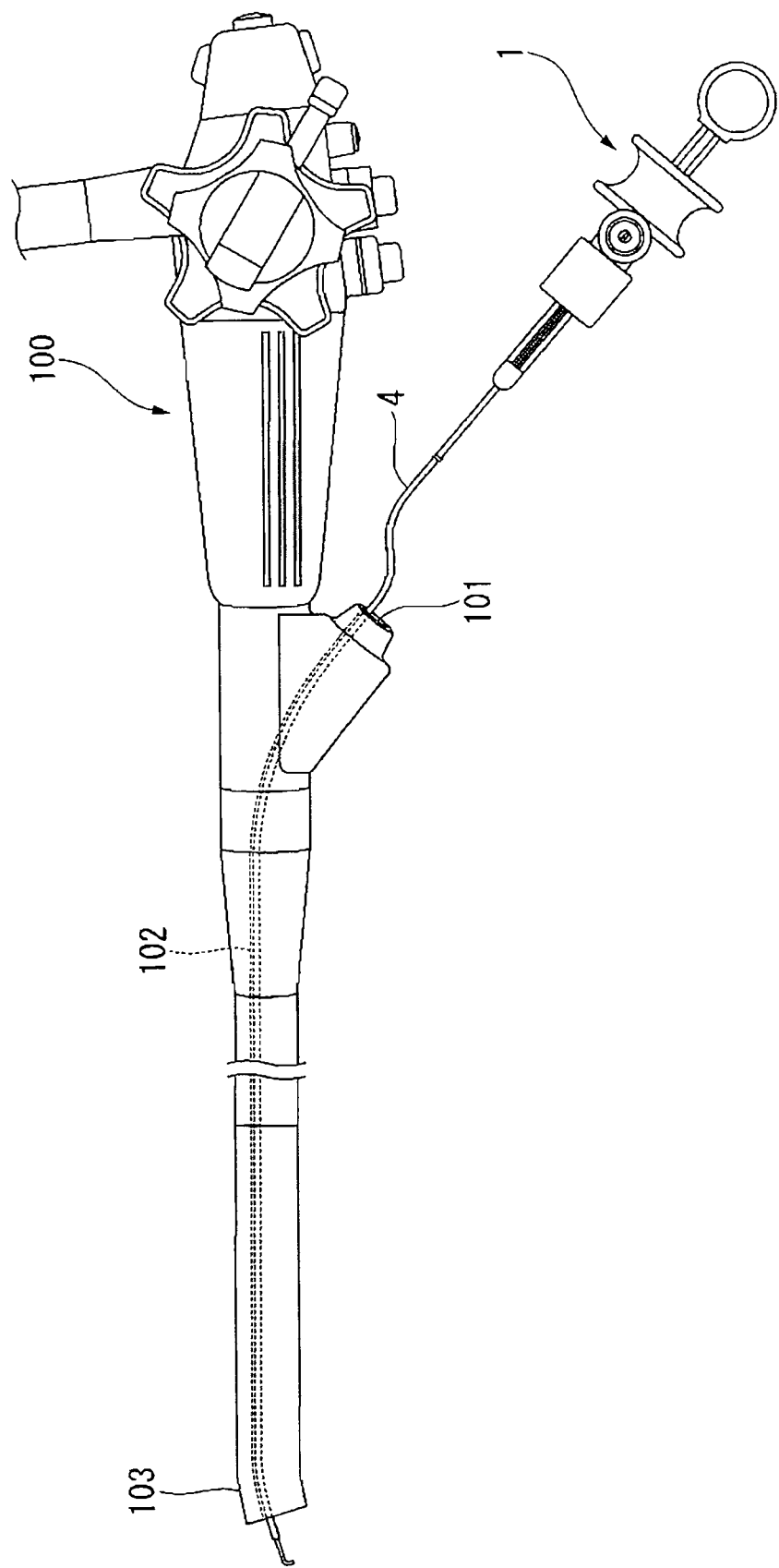
FIG. 4 is a view showing the treatment instrument for endoscopic use inserted into an endoscope.

Placing a user's fingers onto the finger hook section 20 and the handle 10 and bringing the operation member 12 to the handle 10 cause the distal end of the hook knife 2 to be enclosed in the sheath 4. The distal end of the sheath 4 is inserted from a forceps port 101 opening on a maneuvering section of the endoscope 100 into an operation channel 102 as illustrated in FIG. 4, and then the distal end of the sheath is projected from the distal end of an insertion section 103.

Pushing the operation member 12 in the direction of the distal end of the endoscope 100 by the user causes the distal end of the hook knife 2 to be exposed from the sheath 4. Subsequently, an electric power cord, not shown in the drawing, is connected to the distal end of the current-carrying plug 13.

Figure 5:
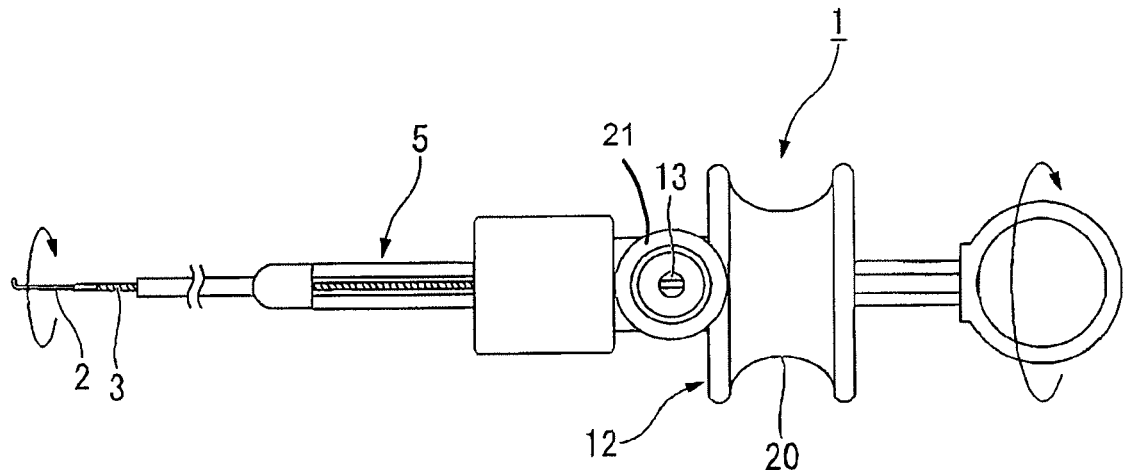
FIG. 5 shows movement while using the treatment instrument for endoscopic use.

The user, upon releasing a finger from the handle 10, rotates the main unit 5 around the axial line direction by a desirable angle with another hand while keeping the finger holding of the finger hook section 20. This results in causing the sliding member 11 and the wire 3 fixed to the sliding member 11 to rotate together with the main unit 5 as shown in FIGS. 2 and 5, thereby rotating the distal end of the hook knife 2 attached to the distal end of the wire 3. The user, in an attempt to direct the distal end of the hook knife 2 in a direction that facilitates intervention, adjusts the rotation of the main unit 5 while observing the distal end of the hook knife 2 on an endoscopically obtained display image.

The operation member 12 capable of freely rotating relative to the main unit 5 and the sliding member 11 does not rotate along with the rotation of the main unit 5. In addition, resilience of a part of the bending line 25A urging the curved surface 25B of the conductive tongue piece 25 of the current-carrying plug 13 toward the sliding member 11 provides regular contact obtains conductivity between the current-carrying plug 13 and the sliding member 11.

After a desirable angle of the distal end of the hook knife 2 is obtained, the power supply is turned on to supply electricity to the hook knife 2 via the current-carrying plug 13, the sliding member 11, and the wire 3, and conducts intervention, e.g., tissue incision, etc. is carried out.

The operation section 6 of the endoscopic-use instrument 1 according to the present embodiment having the operation member 12 capable of freely rotating relative to the sliding member 11 and the main unit 5 in the circumferential direction enables the user with a finger placed on the finger hook section 20 and holding the operation member 12 to rotate the main unit 5 to cause the hook knife 2 to be rotated.

In addition, the current-carrying plug 13 fixed to the operation member 12 prevents a power cable connected to the current-carrying plug 13 from being entangled with the operation member 12 and the main unit 5 while rotating the hook knife 2, thereby, facilitating the rotational operation of the hook knife 2.

In addition, the curved surface 25B of the conductive tongue piece 25 provided to the current-carrying plug 13 urged by resilience produced near the bending lines 25A toward the sliding member 11 keeps contacting the sliding member 11, thereby preventing the distal end of the conductive tongue piece 25 upon operating and rotating the main unit 5 from hooking onto the sliding section 11, and obtaining conductivity between the sliding member 11 and the current-carrying plug 13 for supplying electricity to the hook knife 2.

In addition, the sheath 4 capable of freely rotating connected and relative to the main unit 5 provides smooth rotation to the main unit 5 and the hook knife 2 of the distal end of the wire 3 regardless of a possible case in which significant friction is produced between the inner wall of the operation channel 102 of the endoscope 100 and the outer surface of the sheath 4.

A treatment instrument for endoscopic use provided with the operation section structure according to a second embodiment of the present invention will be explained next with reference to FIGS. 6 to 9. An endoscopic-use instrument 31 according to the present invention differs from the endoscopic-use instrument 1 according to the aforementioned first embodiment based on the configuration of the distal end mechanism, the structure of a handle of the main unit, and the shape of a conductive section. Note that components that are the same as those of the aforementioned endoscopic instrument 1 will be assigned the same numeric symbols and common explanations thereof will be omitted.

Figure 6:
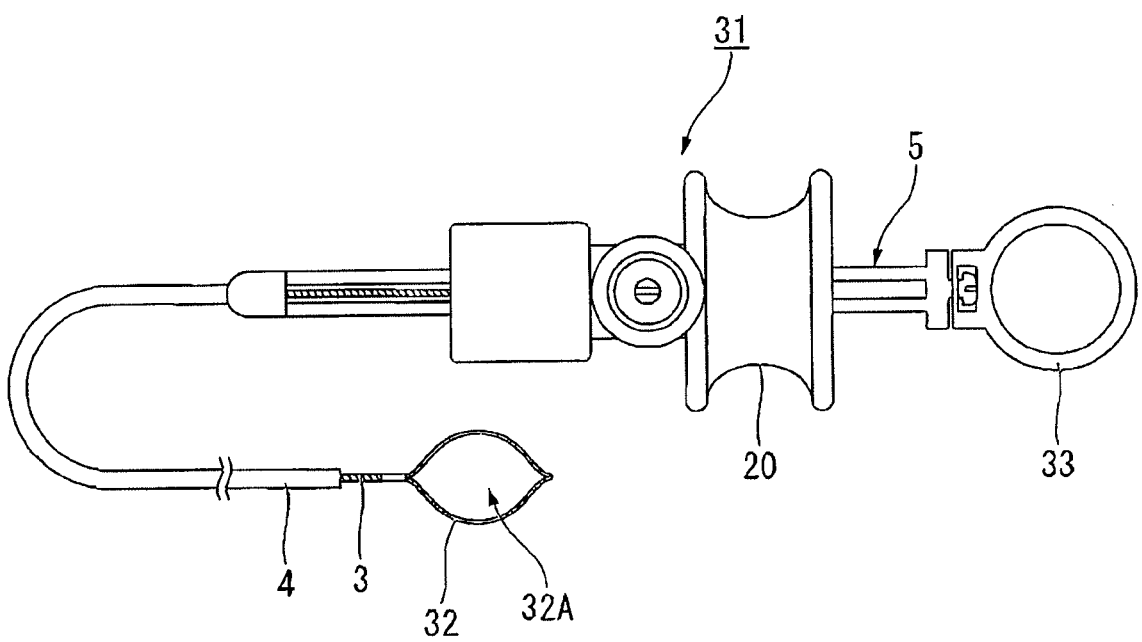
FIG. 6 is a plan view of a treatment instrument for endoscopic use provided with an operation section structure according to a second embodiment of the present invention.

As shown in FIG. 6, the distal end mechanism of the endoscopic-use instrument 31 is a snare loop 32. The end section of the snare loop 32 is connected to the wire 3. In addition, a handle 33 provided to the proximal end of the main unit 5 is attached to be capable of freely rotating around the axial line relative to the main unit 5.

Figure 7:
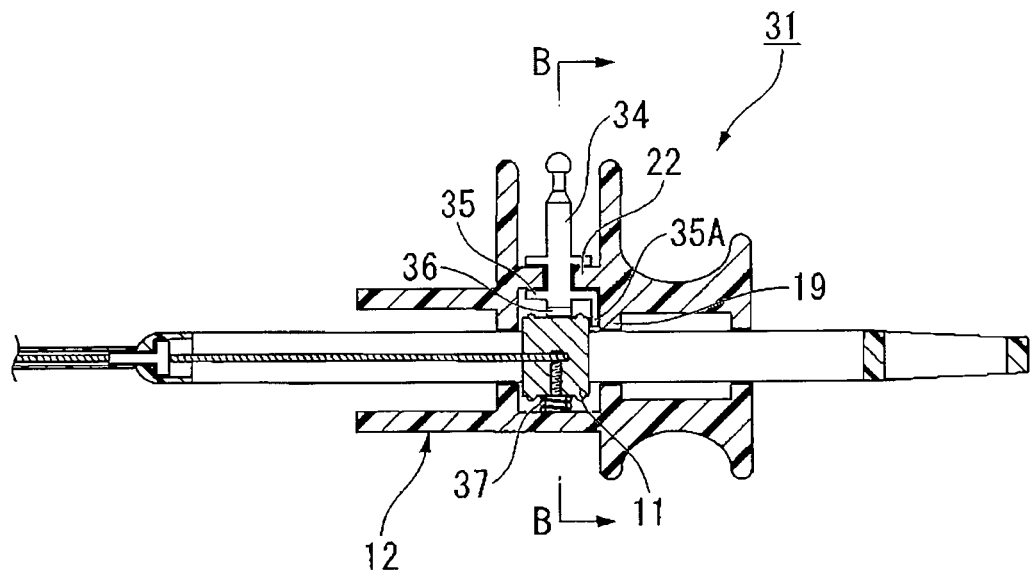
FIG. 7 is a cross sectional view showing the treatment instrument for endoscopic use.

In addition, a current-carrying plug 34 has a fixture section 35 located inward relative to the cylindrical section 22 as shown in FIG. 7. A part of the fixture section 35 bends and extends toward the sliding member 11. A distal end 35A extending from the fixture section 35 enters between the sliding member 11 and the rear wall section 19 of the operation member 12 to make contact with the sliding member 11.

Figure 8:
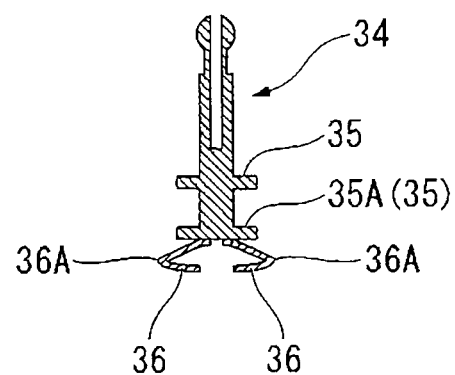
FIG. 8 is a cross-sectional view of a current-carrying plug viewed along the line B-B in FIG. 7.

FIG. 8 is a cross-sectional view of the current-carrying plug 34 viewed along the line B-B in FIG. 7. A pair of conductive tongue pieces 36 are provided to the end section of the current-carrying plug 34 in the vicinity of the sliding member 11. Each conductive tongue piece 36 bends in the vicinity of a midpoint 36A in the same direction as that of the conductive tongue piece 25 of the first embodiment. Each conductive tongue piece 36 making contact with the sliding member 11 in the vicinity of the distal end obtains conductivity.

In addition, a spiral spring 37 provided between a section of the outer periphery of the sliding member 11 opposite to the conductive tongue piece 36 and the cylindrical section 22 urges the sliding member 11 toward the current-carrying plug 34.

Movement of the endoscopic-use instrument 31 having the aforementioned configuration in use will be explained.

In the beginning, an endoscope is maneuvered similarly to the first embodiment to be inserted into a body of a patient etc., and the distal end of the sheath 4 is inserted from a forceps port 101 to project from the distal end of the insertion section 103.

Subsequently, moving the operation member 12 in the distal end direction of the main unit 5 and exposing the snare loop 32 from the sheath 4 causes the snare loop 32 to expand with its own resilience, thereby forming a loop plane 32A as shown in FIG. 6.

Adjusting this state of loop plane 32A into a direction desirable with respect to a target site tissue necessitates rotating the main unit 5. The user using the endoscopic-use instrument 31 of the present embodiment rotates only the main unit 5 by a hand while holding the finger hook section 20 and the handle 33 with the fingers of the other hand.

Figure 9:
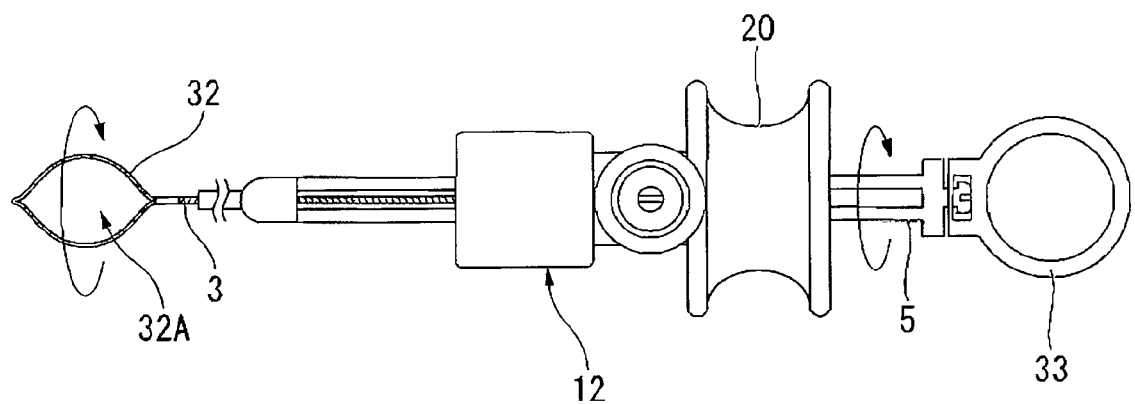
FIG. 9 shows movement while using the treatment instrument for endoscopic use.

This results in causing the main unit 5, the sliding member 1, the wire 3, and the snare loop 32 fixed to the distal end of the wire 3 to rotate unitarily, thereby changing the direction of the loop plane 32A as shown in FIG. 9.

The main unit 5 may be rotated by holding and rotating a section between the operation member 12 and the handle 33, or by holding and rotating a section in the vicinity of the snare loop 32 relative to the operation member 12 as shown in FIG. 9.

The user, upon obtaining a desirable direction of the loop plane 32A with respect to the tissue, conducts intervention by bringing the operation member 12 close to the handle 33 while supplying electricity to the snare loop 32 by the same operation as that of the first embodiment, and by closing the snare loop 32. This state of the fixture section 35 of the current-carrying plug 34 entering between the sliding member 11 and the rear wall section 19 provides reliable conductivity between the current-carrying plug 34 and the sliding member 11.

The endoscopic-use instrument 31 according to the present embodiment has not only the operation member 12 but also the handle 33 that are capable of freely rotating relative to the main unit 5 allows the user to change the direction of the snare loop 32 by rotating only the main unit 5 while holding the finger hook section 20 and the handle 33. Consequently, the direction of the distal end mechanism can be adjusted while fixing the correlation of the sheath 4 relative to the distal end mechanism reliably.

In addition, the fixture section 35 of the current-carrying plug 34 entering between the sliding member 11 and the rear wall section 19 provides reliable conductivity between the current-carrying plug 34 and the sliding member 11 while moving the operation member 12, thereby, enabling intervention using electricity in a stable state.

In addition, the spiral spring 37 provided between the section of the outer periphery of the sliding member 11 opposite the conductive tongue piece 36 and the cylindrical section 22 equalizes the force of the conductive tongue piece 36 pushing the sliding member 11 with the force of the spiral spring 37 which is in-turn pushing the sliding member 11, thereby, restricting axial deviation of the sliding member 11 relative to the main unit 5 and preventing the sliding member 11 from wobbling, etc.

A treatment instrument for endoscopic use provided with the operation section structure according to a third embodiment of the present invention will be explained next with reference to FIGS. 10 to 12. An endoscopic-use instrument 41 according to the present invention differs from the endoscopic-use instrument 1 according to the aforementioned first embodiment based on the configuration of the distal end mechanism, the use of two components to form a sliding member, and the shape of a conductive section.

Note that components that are the same as those of the aforementioned endoscopic instrument 1 will be assigned the same numeric symbols and common explanations thereof will be omitted.

Figure 10:
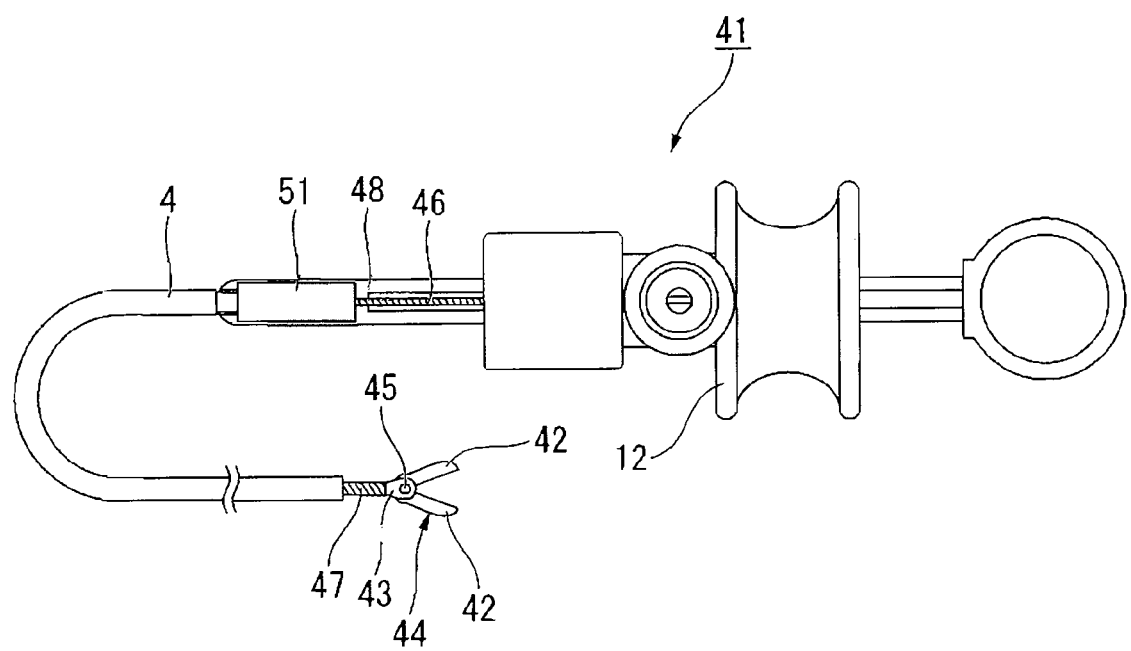
FIG. 10 is a plan view of a treatment instrument for endoscopic use provided with an operation section structure according to a third embodiment of the present invention.

As shown in FIG. 10, the distal end mechanism of the endoscopic-use instrument 41 is a commonly known configuration of a high-frequency forceps 44 having a pair of forceps members 42 and a support member 43 supporting each forceps member 42 rotatably. The support member 43 using a pin 45 supports each freely rotatable forceps member 42. A wire 46 according to the present embodiment includes two stranded metal wires. The tip of each wire is connected to the proximal end of each forceps member 42. That is, extending or retracting the wire 46 allows the pair of forceps members 42 to open or close in configuration.

The support member 43 is fixed to the distal end of a coil sheath 47 formed by densely wound metal wires by means of laser welding, brazing, soldering, or crimping, etc. The wire 46 is inserted through the coil sheath 47, and the coil sheath 47 is inserted through the sheath 4.

Figure 11:
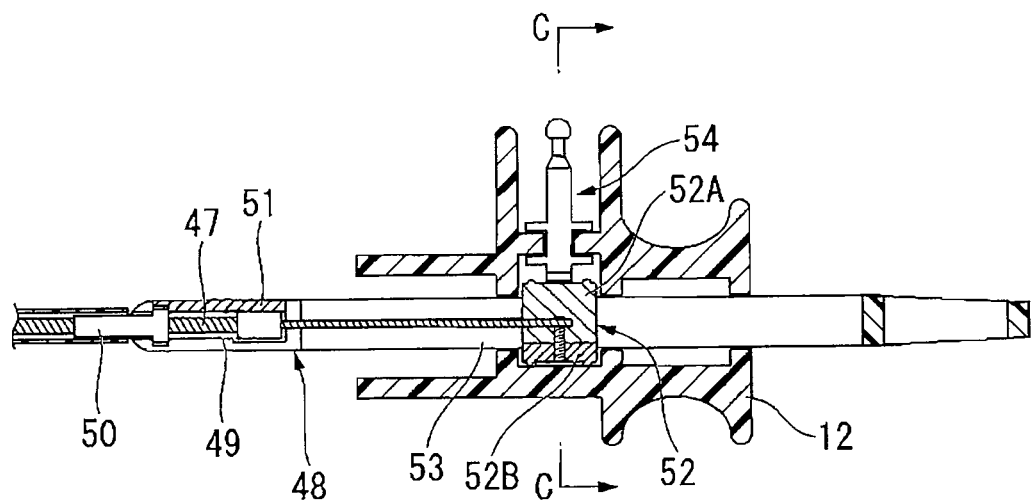
FIG. 11 is a cross sectional view showing the treatment instrument for endoscopic use.

As shown in FIG. 11, the proximal end of the coil sheath 47 is fixed to a fastening groove 49 provided to the distal end of a main unit 48. Also, the coil sheath 47 incapable of rotating relative to the main unit 48 is fixed to a T-letter-shaped member 50 inserted proximally. That is, rotating the main unit 48 causes the coil sheath 47 to rotate accordingly. A cover 51 covers the coil sheath 47 and the T-letter-shaped member 50 that are disposed in the fastening groove 49.

A sliding member 52 according to the present embodiment has an outline that is the same as that of the sliding member 11 according to the first embodiment. As shown in FIG. 11, a first member 52A and a second member 52B are disposed to place a lateral wall section 53 therebetween vertically in configuration.

Figure 12:
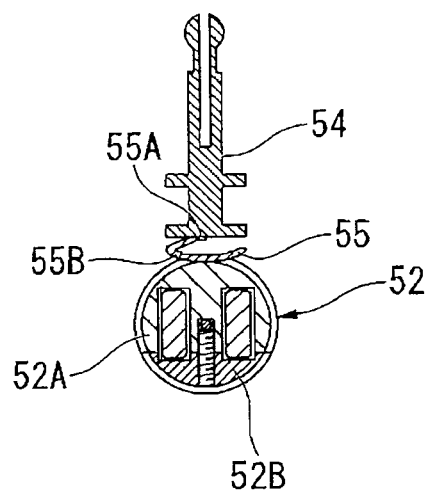
FIG. 12 is a cross-sectional view of a current-carrying plug and a sliding member along the line C-C in FIG. 11.

FIG. 12 is a cross-sectional view of the sliding member 52 and a current-carrying plug 54 viewed along the line C-C in FIG. 11.

The present embodiment has a conductive tongue piece 55. The conductive tongue piece 55 fixed to the lower end of a proximal end 55A of the current-carrying plug 54 extends outward in the width direction of the sliding member 52. Bending work provided to the folded end section forms a downward projecting curved surface 55B. The conductive tongue piece 55 making contact with the sliding member 52 on the curved surface 55B obtains conductivity.

The endoscopic-use instrument 41 according to the present embodiment provided with the coil sheath 47 incapable of rotating relative to the main unit 48 fixed to the T-letter-shaped member 50 can adjust the direction of the distal end mechanism, e.g., the high-frequency forceps 44 using a coil sheath by rotating the main unit 48 without re-grasping the operation member 12.

In addition, the conductive section formed by fixing only either one of the end sections 55A of the conductive tongue piece 55 provides a simple structure to the current-carrying plug 54.

The technical scope of the present invention is not limited to the embodiments described above. Rather, various modifications may be added unless deviating from the spirit of the invention.

Figure 13:
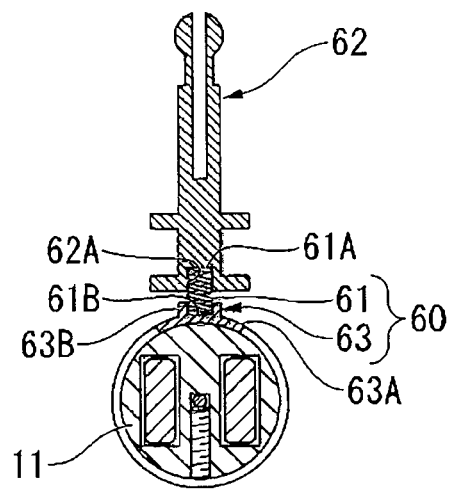
FIG. 13 is a cross-sectional view of a current-carrying plug and a sliding member in a modified example of the present invention.

The aforementioned embodiments each explained with reference to examples using a conductive plate material for a conductive section may be replaced by a modified example using a conductive section 60 including a spiral spring (spring) 61 made of a conductive material as shown in FIG. 13. Providing a recessed section 62A for enclosing an end section 61A of the spiral spring 61 to the current-carrying plug 62 and disposing a conductive member 63 having a substantial arch contact surface 63A and a cylindrical section 63B for enclosing the other end section 61B of the spiral spring between the spiral spring 61 and the sliding member 11 provide reliable conductivity between the sliding member 11 and the current-carrying plug, and a stable conductive section in configuration.

Alternatively, the recessed section 62A or the conductive member 63 may not be provided, and the conductive section 60 may be formed by only the spiral spring 61.

In contrast to each aforementioned embodiment explained with reference to the examples provided with the current-carrying plug, a current-carrying plug may be omitted and not be provided to a treatment instrument for endoscopic use provided with a distal end mechanism in no need of conductivity.

In addition, each embodiment does not limit the distal end mechanism. The operation section structure according to the present invention is adaptable to any distal end mechanism requiring rotation for the desirable positioning thereof.

Furthermore, each aforementioned embodiment explained with reference to the example associated with a lateral wall section forming the main unit almost fully may be replaced by a configuration using a main unit having a shape, e.g., appropriate thickness, that facilitates the holding of a constant proximal or distal portion of a operating member and allowing a sliding member to slide on the rest of the portion. This results in facilitating the rotational operation of the distal end mechanism.

The present invention is not limited to the above descriptions but is limited only by the appended claims.

What is claimed is:

1. A treatment instrument for endoscopic use comprising:
   a distal end mechanism adapted to be inserted into a body cavity for conducting various interventions;
   a wire, a distal end of which is connected to the distal end mechanism;
   a tubular flexible sheath, into which the wire is inserted;
   a main unit connected to a base end of the sheath;
   an operation section provided on the main unit, the operation section having:
   a sliding member provided on the main unit slidably in a longitudinal direction thereof, the sliding member fixed to a base end of the wire, and the main unit inserted through the sliding member;
   an operation member provided on the sliding member rotatably in a circumferential direction thereof, the operation member configured to rotate and advance/retract relative to the main unit; and
   a current-carrying section fixed to the operation member;
   the treatment instrument being configured to be capable of being operated by a single operator.

2. The treatment instrument for endoscopic use according to claim 1, wherein a handle, capable of freely rotating around the main unit as a rotational axis, is provided to a proximal end of the main unit.

3. The treatment instrument for endoscopic use according to claim 2,
wherein the current-carrying section has a conductive section, and the conductive section is formed by bending a conductive plate material having bending lines extending in a sliding direction of the sliding member.

4. The treatment instrument for endoscopic use according to claim 2,
wherein the current-carrying section has a conductive section, and the conductive section is formed to include a spring made of a conductive material.

5. The treatment instrument for endoscopic use according to claim 1,
wherein the current-carrying section has a conductive section, and the conductive section is formed by bending a conductive plate material having bending lines extending in a sliding direction of the sliding member.

6. The treatment instrument for endoscopic use according to claim 1,
wherein the current-carrying section has a conductive section, and the conductive section is formed to include a spring made of a conductive material.

7. The treatment instrument for endoscopic use according to claim 1, further comprising:
a coil sheath which is disposed inward relative to the sheath and outward relative to the wire, a distal end of which is fixed to the distal end mechanism, and a proximal end of which has the coil sheath fixed to the main unit and is incapable of rotating.

8. The treatment instrument for endoscopic use according to claim 1,
wherein the operation member has a front wall section provided at a distal end side of the operation member, and a rear wall section provided at a proximal end side of the operation member, the front wall section and the rear wall section fix the sliding member therebetween.

9. The treatment instrument for endoscopic use according to claim 1, wherein the sliding member has a sliding hole which extends therethrough in the longitudinal direction, and which is configured to receive the main unit.

* * * * *